United States Patent [19]
Whalen

[11] Patent Number: 5,171,207
[45] Date of Patent: Dec. 15, 1992

[54] APPARATUS AND METHOD OF USE FOR PULSATILE BLOOD FLOW

[75] Inventor: Robert L. Whalen, Cambridge, Mass.

[73] Assignee: Whalen Biomedical, Inc., Cambridge, Mass.

[21] Appl. No.: 679,790

[22] Filed: Apr. 3, 1991

[51] Int. Cl.5 .............................................. A61M 1/10
[52] U.S. Cl. ...................................... 600/16; 600/18; 417/394
[58] Field of Search ........................... 600/16, 17, 18; 417/394

[56] References Cited

U.S. PATENT DOCUMENTS

| | | | |
|---|---|---|---|
| 4,116,589 | 9/1978 | Rishton | 600/18 |
| 4,240,409 | 12/1980 | Robinson et al. | 600/16 |
| 4,250,872 | 2/1981 | Tamari | 600/16 |
| 4,573,883 | 3/1986 | Noon et al. | 600/16 |

OTHER PUBLICATIONS

Frater, et al., "Pulsatile Cardiopulmonary Bypass: Failure to ... or Hormones", *Circulation* 62 (Suppl. I), 1980, I19-I25.

Bregman, et al., "Counterpulsation with a New Pulsatile ... Open-Heart Surgery", *Medical Instrumentation*, 10, (1976), 232-238.

Bregman, "Clinical Experience with a New Pulsatile ... Open-Heart Surgery", *Artificial Organs* 2, (1978) 244-248.

Yukihio Nose et al. "Experimental Use of an Electrochemically Controlled Prosthesis as an Auxillary Left Ventricle", IX *Trans Amer. Soc. Artif. Int. Organs* 269-272 (1963).

Whalen et al. "A New Right Ventricular Assist Device The Extracorporeal Assist Device (EPAD)" 10 ASSAIO 222-226 (1987).

*Primary Examiner*—Kyle L. Howell
*Assistant Examiner*—Scott M. Getzow
*Attorney, Agent, or Firm*—Lorusso & Loud

[57] ABSTRACT

An apparatus and a method of use are disclosed which assist in pulsating blood to a patient during cardiopulmonary bypass surgery and assists in weaning a patient after cardiopulmonary bypass surgery by counterpulsating. The apparatus includes a blood pump with a collapsible bladder and a bladder support ring with a plurality of openings to permit the entering of continuous flowing blood, the exiting of a pulsatile blood flow and the release of any air bubbles trapped within the blood supply. The pulsating blood flow is created by the compression of the collapsible bladder when filled with blood. The method consist of connecting the apparatus to the aortic return line of a cardiopulmonary bypass circuitry and to the aortic cannula of the patient. The apparatus is positioned near to the patient to maximize pulsatile output. Compression of the bladder can be synchronized to create the physiologic blood pressure of the patient or to counterpulsate with the patient's heart.

25 Claims, 1 Drawing Sheet

APPARATUS AND METHOD OF USE FOR PULSATILE BLOOD FLOW

LICENSE RIGHTS

The U.S. government has a paid up license in this invention and the right in limited circumstances to require the patent owner to license others on reasonable terms as provided by the terms of SBIR Phase II Grant 2 R44HL35936 awarded by National Heart, Lung and Blood Institute of the National Institutes of Health.

BACKGROUND OF THE INVENTION

This invention relates generally to a blood pump and method or use and more specifically to an apparatus and method for providing to a patient a pulsating or counterpulsating blood flow at the proximal end of an aortic line of a cardiopulmonary bypass circuitry.

Developments in surgical techniques has caused cardiopulmonary bypass surgery to become a more widely practiced surgical procedure. During cardiopulmonary bypass surgery the heart is stopped and the blood is taken from the venous system and run through a pump oxygenating system and put back into the aorta, thus bypassing the heart and lungs. Typically this flow is non-pulsatile. Alternatively, roller pumps or centrifugal pumps are utilized to create some sort of rhythmic blood supply. These pumps must be placed at the distal end of the aortic line thereby attenuating any pulse which may have been created, resulting in a somewhat steady flow of blood back to the patient. Establishing a steady flow of blood during coronary bypass has been implicated in fluid accumulation in the lungs and brain and in myocardial strain caused by increased afterload and is therefore undesirable.

Pulsatile blood pumps have been utilized during such operations. The only pulsatile device actually used during surgery was the PAD, a device manufactured by the Datascope Corporation. It was a device placed in the return line to the patient, but not in close proximity to the aortic cannula. Its performance was thus limited. The pulsatile device of U.S. Pat. No. 4,240,409 to Robinson et al was designed as a device for postsurgical use and not during the actual surgery. This type of device is invasive. These types of blood pumps both receive the pulsating blood directly from the blood vessel and must likewise discharge the blood in a pulsating fashion. Sometimes the blood both enters and is discharged through the very same conduit.

Once the patient has undergone cardiopulmonary bypass surgery, patients are normally weaned by decreasing the bypass flow rate and letting the patient's heart assume more and more of the total blood flow. If there is difficulty, pharmacologic support is first employed, if this is unsuccessful, a device called an intraaortic balloon pump is generally used to assist the heart by producing counterpulsation. Counterpulsation is a way to "unload" the heart by lessening the systolic pressure. The balloon pump has been the simplest of all assist devices. The balloon is inserted into the aorta either directly or through the femoral artery. The balloon is collapsed during the ejection of blood from the heart, lowering the aortic pressure and then expanded during the period of filling of the heart to provide diastolic augmentation. This assist device involves additional invasive techniques on a patient that has already been through surgery.

A new apparatus and method to provide pulsatile blood flow that would simulate the patient's own blood pressure and aide in the weaning of patients after cardiopulmonary bypass surgery by providing counterplusatile blood flow will be welcomed in the area of cardiopulmonary bypass surgery. Benefits of such an inovation are decreased catecholamine stress response to cardiopulmonary bypass, reduced fluid overloading resulting from improved renal function and improved postoperative recovery as measured by postoperative tracheal intubation time.

SUMMARY OF THE INVENTION

In accordance with the present invention an apparatus and method is disclosed for providing a pulsatile blood flow during cardiopulmonary bypass surgery. The apparatus includes a blood pump with a collapsible bladder and a bladder support ring which secures the bladder in place and has both an inlet for the entrance of continuous blood flow and an outlet for the exiting of pulsatile blood flow to the patient. When the bladder is filled with incoming blood, pressure is applied to the bladder which compresses the bladder and thereby forces the blood through the outlet back into the patient's circulatory system in the same fashion as the patient's heart. The bladder also acts as a bubble trap so that air can be removed from the blood, prior to pulsation, via a sealable valve. The most efficient method for providing a pulsatile blood supply to a patient is to connect the inlet of the blood pump to the proximal end of the aortic line of a cardiopulmonary bypass circuitry. With this arrangement the outlet is near the patient and is connected directly to the aortic cannula. This has the added advantage that the pulsated flow of blood does not have to go through the entire outflow circuitry of the cardiopulmonary bypass system before it enters the patient and therefore provides a strong pulsatile flow of blood back to the patient.

At the end of cardiopulmonary bypass surgery, the blood pump can be used to provide counterpulsation directly once the patient's heart has been re-started. In accordance with the present invention, the blood pump uses the aortic cannula used for the bypass circuitry, so it may be used immediately and without additional surgical procedures to provide counterpulation.

Accordingly, an object of this invention is to provide an apparatus for producing pulsatile blood flow which mimicks the flow of blood from a patient's heart.

A further object of the invention is to provide an apparatus for pulsatile blood flow which acts as a bubble trap.

It is yet another object of the invention to provide a device for providing pulsatile blood flow which can be located proximate to the cannulation means used in bypass surgery.

It is still another object of the invention to provide a method for producing pulsatile blood flow which decreases hormone levels and interoperative stress.

It is an additional object of the invention to provide a method for mechanically producing pulsatile blood flow which closely resembles physiologic blood pressure for the patient.

It is still a further object of the invention to provide a method for producing counterpulsatile blood flow which lowers the pressure the heart must create during contraction.

DESCRIPTION OF THE PREFERRED EMBODIMENTS

At the outset, the invention is described in its broadest overall aspects with a more detailed description following. The broadest overall aspects of the invention involve a pulsatile blood pump which mechanically pumps blood in a manner similar to a patient's own heart. The blood pump has a collapsible bladder and a bladder support ring with a plurality of openings which allow the entering of blood and the exiting of pulsated blood from the blood pump and in addition allows air to be removed from the blood prior to recirculating through the patient. The method of using the apparatus involves positioning the pulsatile blood pump at the proximal end of the aortic line of a cardiopulmonary bypass circuitry and also adjacent to the patient's aortic cannula, thus enabling maximal pulsatile efficiency.

Figure 1:
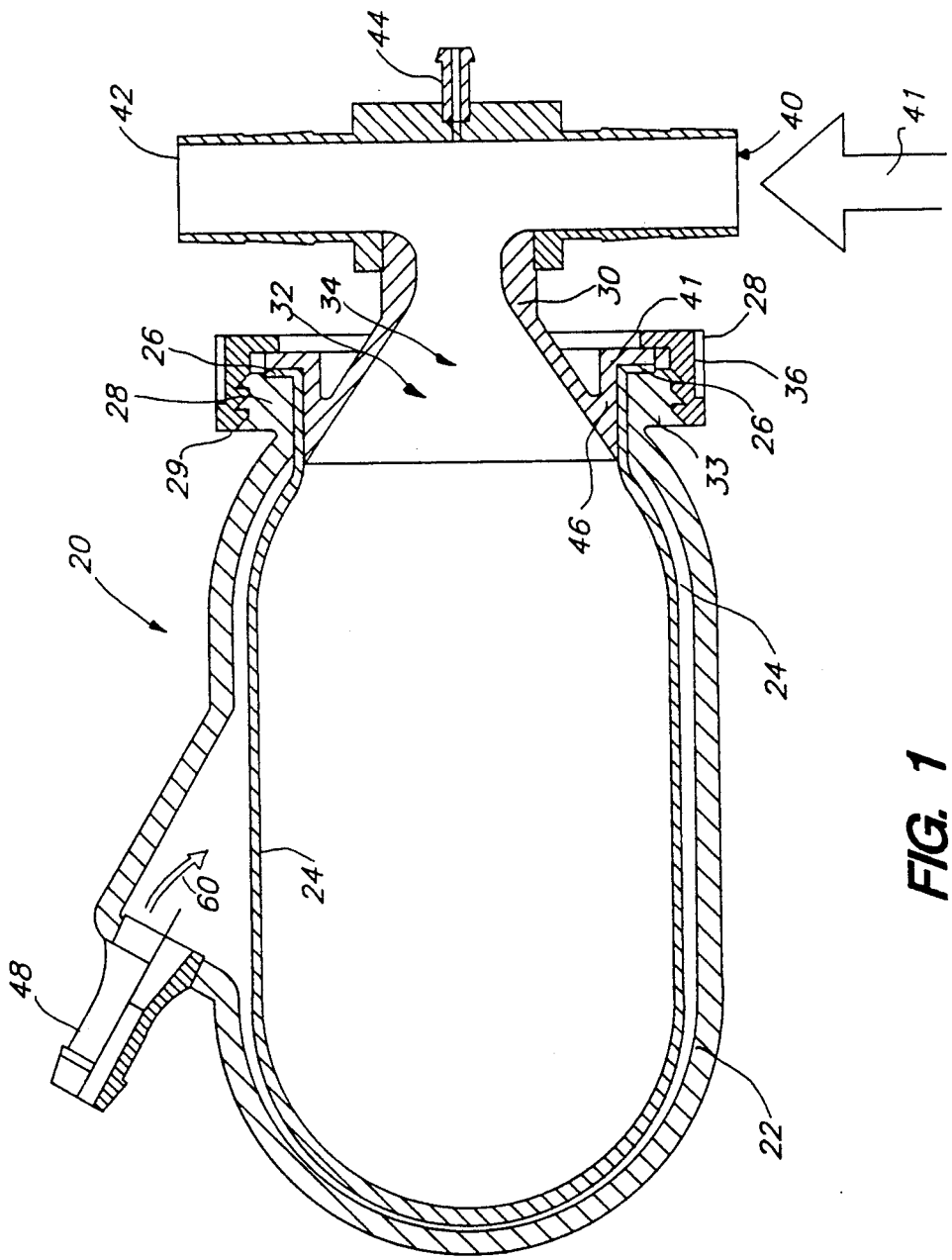
FIG. 1 is a cross-sectional view of the pulsatile blood pump used in accordance with the present invention.

In the preferred embodiment of the blood pump of the present invention as shown in FIG. 1, the pulsatile blood pump 20 comprises a solid housing 22, which may be made of blow molded polymeric material, within which a bladder 24 snugly fits. The bladder 24, which may be made of silcone rubber, has a 3-lobe non-occulsive pattern to minimize blood damage and has a lip 26 which lays atop of a lip 28 of the housing 22.

Figure 2:
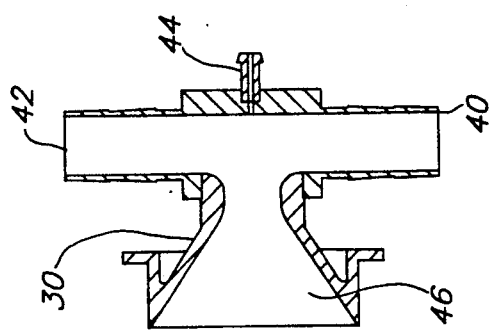
FIG. 2 is a cross-sectional view of the bladder support ring included in the pump of FIG. 1.

A bladder support ring 30, as seen more clearly in FIG. 2 fits firmly within both opening 32 of the bladder and opening 34 of the housing. A conduit or neck portion 46 of bladder support ring 30 secures the bladder 24 in place and is sealed by a screw ring 36 which is attached to the housing neck 38. In the preferred embodiment, bladder support ring 30 has three openings, inlet 40, outlet 42 and a sealable opening or vent 44.

Blood enters the bladder 24 through the inlet 40 of the bladder support ring 32 as shown by arrow 41. As the blood is trapped within the bladder 24, air may be removed through sealable opening 44. A conventional stop cock, not shown, may be used to open and close sealable opening 44. Once the bladder 24 is filled with incoming blood, pressure, such as air pressure, is applied to the bladder through port 48 of the housing 22. The blood pump 20 is designed so that when screw ring 36 is tightened onto threads 29 with the lip 26 of bladder 24 sandwiched between housing lip 28 and a flange 41 or ring 30, a sealed state exists which causes a pressure increase through drive line 48 as shown by arrow 50 to collapse the bladder 24. The source of pressure, not shown, may be an air pump. As the pressure is applied to bladder 24, the bladder 24 collapses and the blood is forced through outlet 4 of the bladder support ring 30. The pulsated blood does not exit through the inlet 4 of the bladder support ring 30 due to the continued pressure exerted through inlet 40 from the incoming blood supply.

The present invention is also concerned with the optimal method of use for the apparatus. In carrying out the invention, the blood pump 20, set forth above, is positioned at the proximal end of the aortic line from the cardiopulmonary bypass circuitry, near the patient. The blood pump 20 is connected to the end of the cardiopulmonary bypass circuitry via inlet 40 of the bladder ring support 30. The compression of the bladder 24, which results in a pulsatile blood flow to the patient through outlet 42, can be regulated by mechanical means to be in synch with the patient's own blood pressure thereby maintaining the physiological conditions of the patient.

The above-stated device can be used to wean a patient from cardiopulmonary bypass. The blood pump 20 is connected to the circuitary and the patient as discussed above and is used for counterpulastion by clamping the circuitary tubing which is connected to the inlet 40. That is, as the heart is contracting, the blood pump 20 is filling with blood through outlet 42, lowering the arterial pressure. Then when the heart is filling, the blood pump 20 ejects blood to the patient through outlet 42, and so the blood pump rather than the heart creates the higher pressure that is measured in the arterial system. This system lowers the pressure work done by the heart during pumping and also incresase the blood flow to the heart muscle.

While the foregoing invention has been described with references to its preferred embodiments, it should not be limited to such embodiments since various alterations and modifications will occur to those skilled in the art. For example, the bladder support ring 32 may have more or less than three openings. All such variations and modifications are intended to fall within the scope of the appended claims.

What is claimed is:

1. An apparatus for pulsating blood comprising:
   a blood pump having a collapsible bladder which has an opening for allowing the entrance of flowing blood and exiting of pulsated blood and a solid housing with a first opening through which said bladder fits within said housing, said housing having a second opening connected to means for pulsating said bladder;
   a bladder support ring which holds said bladder in place within said housing, said bladder support ring having a plurality of openings for the entrance of flowing blood and the exiting of pulsated blood; and
   means for sealing said bladder support ring which creates an air tight system between said bladder and said solid housing.

2. The apparatus of claim 1 wherein said bladder support ring consists of two openings said, openings being an inlet and an outlet valve for the entering and exiting of blood.

3. The apparatus of claim 2 wherein said bladder support ring further comprises a third opening for the release of air bubbles.

4. The apparatus of claim 3 wherein said third opening has means for opening and closing.

5. The apparatus of claim 1 wherein said collapsible bladder comprises a 3-lobe non-occlusive collapse pattern of silicone rubber.

6. The apparatus of claim 1 wherein said means for pulsating the bladder comprises an air pump which compresses the bladder when air is applied.

7. The apparatus of claim 1 wherein said means for sealing said bladder support ring comprises a screw ring bladder support ring which is tightened onto threads of a lip of said solid housing.

8. A method for pulsating blood in a cardiopulmonary bypass circuitry comprising:
   attaching an inlet opening from a blood pump having a collapsible bladder within a solid housing to the proximal end of an aortic line of a cardiopulmonary bypass circuitry;

attaching an outlet opening from said blood pump to an aortic cannula of a patient;

pulsating blood from said blood pump to said patient in synch with the patient's physiological blood pressure.

9. The method of 8 further comprising releasing air bubbles from said blood pump prior to pulsating blood to said patient.

10. The method as set forth in claim 9 wherein the blood is pulsated by compressing the collapsible bladder when filled with blood.

11. The method as set forth in claim 9 including the step of positioning of a blood pump proximate to said patient.

12. The method of claim 9 including the step for weaning a patient after cardiopulmonary surgery by clamping between the aortic line of the cardiopulmonary bypass circuitry and the inlet opening from said blood pump.

13. The method as set forth in claim 12 wherein the blood is pulsated by compressing the collapsible bladder when filled with blood.

14. The method of claim 12 including the step of counterpulsating the blood to effect weaning.

15. The method as set forth in claim 14 including the step of positioning of a blood pump proximate to said patient.

16. The method as set forth in claim 12 including the step of positioning of a blood pump proximate to said patient.

17. The method as set forth in claim 14 wherein the blood is pulsated by compressing the collapsible bladder when filled with blood.

18. The method of claim 8 including the step for weaning a patient after cardiopulmonary surgery by clamping between the aortic line of the cardiopulmonary bypass circuitry and the inlet opening from said blood pump.

19. The method of claim 18 including the step of counterpulsating the blood to effect weaning.

20. The method as set forth in claim 19 wherein the blood is pulsated by compressing the collapsible bladder when filled with blood.

21. The method as set forth in claim 19 including the step of positioning of a blood pump proximate to said patient.

22. The method as set forth in claim 18 including the step of positioning of a blood pump proximate to said patient.

23. The method as set forth in clair 18 wherein the blood is pulsated by compressing the collapsible bladder when filled with blood.

24. The method as set forth in claim 8 including the step of positioning of a blood pump proximate to said patient.

25. The method as set forth in claim 8 wherein the blood is pulsated by compressing the collapsible bladder when filled with blood.

* * * * *